US011678990B2

(12) United States Patent
Whitwell et al.

(10) Patent No.: US 11,678,990 B2
(45) Date of Patent: Jun. 20, 2023

(54) DEVICE FOR FACILITATING THE FORMATION OF NEW BONE TISSUE

(71) Applicants: ADLER ORTHO S.P.A., Cormano (IT); I-ETHOS MEDICAL LTD, Buckinghamshire (GB)

(72) Inventors: Duncan Whitwell, Oxford (GB); Adrian Taylor, Oxford (GB); Ben Kendrick, Oxford (GB); Deborah Higgs, London (GB); Mark Falworth, Surrey (GB); Max Gibbons, Oxford (GB); Tom Cosker, Sussex (GB); Mike Parry, Worcestershire (GB); Jonathan Stevenson, West Midlands (GB); Andy Johnston, London (GB); Scott Sommerville, Queensland (AU); Luke Johnson, South Australia (AU); Richard Boyle, New South Wales (AU); Gordon Blunn, Hertfordshire (GB); Solomon Dadia, Rosh Ha'ayin (IL); Panos Gikas, London (GB)

(73) Assignees: ADLER ORTHO S.P.A., Cormano (IT); I-ETHOS MEDICAL LTD, Buckinghamshire (GB)

( * ) Notice: Subject to any disclaimer, the term of this patent is extended or adjusted under 35 U.S.C. 154(b) by 0 days.

(21) Appl. No.: 17/258,530

(22) PCT Filed: Jun. 12, 2019

(86) PCT No.: PCT/EP2019/065400
§ 371 (c)(1),
(2) Date: Jan. 7, 2021

(87) PCT Pub. No.: WO2020/011475
PCT Pub. Date: Jan. 16, 2020

(65) Prior Publication Data
US 2021/0228362 A1 Jul. 29, 2021

(30) Foreign Application Priority Data

Jul. 10, 2018 (IT) .................. 102018000007049

(51) Int. Cl.
*A61F 2/30* (2006.01)
*A61F 2/42* (2006.01)
(Continued)

(52) U.S. Cl.
CPC .............. *A61F 2/28* (2013.01); *A61B 17/72* (2013.01); *A61F 2/30771* (2013.01);
(Continued)

(58) Field of Classification Search
CPC .... A61F 2/28; A61F 2/30756; A61F 2/30734; A61F 2/4618; A61F 2/30749;
(Continued)

(56) References Cited

U.S. PATENT DOCUMENTS 5,364,400 A * 11/1994 Rego, Jr. ................ A61L 31/10
606/77
5,683,463 A * 11/1997 Godefroy ............... A61F 2/446
623/17.16
(Continued)

FOREIGN PATENT DOCUMENTS

EP 1527741 A1 * 5/2005 ............ A61B 17/68
EP 1527741 A1 5/2005
(Continued)

OTHER PUBLICATIONS

International Search Report dated Sep. 5, 2019 re: Application No. PCT/EP2019/065400, pp. 1-4, citing: EP 1 527 741 A1, WO 2009/053690 A2, WO 2009/143374 A2, US 2008/0027558 A1 and U.S. Pat. No. 6,783,549 B1.
(Continued)

*Primary Examiner* — Ann Schillinger
(74) *Attorney, Agent, or Firm* — Cantor Colburn LLP

(57) ABSTRACT

A device for facilitating the formation of new bone tissue includes a body that defines an upper portion and a lower portion, the lower portion having a substantially frustum-like shape, the upper portion having a substantially cylindrical shape. The lower portion is adapted to be inserted into the medullary canal of a bone.

4 Claims, 3 Drawing Sheets

(51) Int. Cl.
*A61B 17/70* (2006.01)
*A61F 2/28* (2006.01)
*A61B 17/72* (2006.01)

(52) U.S. Cl.
CPC .......... *A61F 2002/3021* (2013.01); *A61F 2002/3093* (2013.01); *A61F 2002/30112* (2013.01); *A61F 2002/30217* (2013.01); *A61F 2002/30784* (2013.01); *A61F 2002/30985* (2013.01); *A61F 2310/00796* (2013.01)

(58) Field of Classification Search
CPC .......... A61F 2/4081; A61F 2002/30205; A61F 2002/2835; A61F 2002/30736; A61F 2/40; A61F 2/30771; A61F 2002/30112; A61F 2002/3021; A61F 2002/30217; A61F 2002/30784; A61F 2002/3093; A61F 2002/30985; A61F 2310/00796; A61F 2/2814; A61F 2002/30064; A61F 2002/30224; A61F 2002/30233; A61F 2002/30738; A61F 2002/3092; A61F 2/30767; A61F 2/30724; A61B 17/72; A61B 17/68

See application file for complete search history.

(56) References Cited

U.S. PATENT DOCUMENTS

| | | | |
|---|---|---|---|
| 6,783,549 B1 | 8/2004 | Stone et al. | |
| 8,926,670 B2 * | 1/2015 | Jackson | A61B 17/704 606/264 |
| 8,998,959 B2 * | 4/2015 | Jackson | A61B 17/7037 606/267 |
| 10,052,178 B2 * | 8/2018 | Kim | A61C 8/0025 |
| 10,194,951 B2 * | 2/2019 | Jackson | A61B 17/7037 |
| 10,307,188 B2 * | 6/2019 | Harshman | A61B 17/1717 |
| 10,806,495 B2 * | 10/2020 | Jackson | A61B 17/7076 |
| 2004/0193268 A1 * | 9/2004 | Hazebrouck | A61F 2/30721 623/16.11 |
| 2006/0167555 A1 * | 7/2006 | Heck | A61F 2/3672 623/20.35 |
| 2006/0167560 A1 * | 7/2006 | Heck | A61F 2/384 623/23.46 |
| 2008/0027558 A1 | 1/2008 | Palmer et al. | |
| 2009/0222007 A1 * | 9/2009 | Aquilo | A61F 2/3609 606/62 |
| 2013/0238036 A1 * | 9/2013 | Sinha | A61B 17/88 606/317 |
| 2014/0081409 A1 * | 3/2014 | James | A61F 2/30734 623/20.15 |
| 2016/0045323 A1 * | 2/2016 | Kovacs | A61F 2/4081 623/19.11 |
| 2016/0302930 A1 * | 10/2016 | Axelrod | A61F 2/3094 |

FOREIGN PATENT DOCUMENTS

| | | | | |
|---|---|---|---|---|
| EP | 2106767 A1 * | 10/2009 | | A61C 8/0012 |
| WO | 2009053690 A2 | 4/2009 | | |
| WO | 2009143374 A2 | 11/2009 | | |
| WO | WO-2009143374 A2 * | 11/2009 | | A61B 17/7208 |

OTHER PUBLICATIONS

IT Search Report dated Mar. 8, 2019 re: Application No. IT 201800007049, pp. 1-7, citing: EP 1 527 741 A1, WO 2009/053690 A2, WO 2009/143374 A2, US 2008/0027558 A1 and U.S. Pat. No. 6,783,549 B1.

Written Opinion dated Sep. 5, 2019 re: Application No. PCT/EP2019/065400, pp. 1-5, citing: EP 1 527 741 A1, WO 2009/053690 A2, WO 2009/143374 A2, US 2008/0027558 A1 and U.S. Pat. No. 6,783,549 B1.

European Office Action for European Application No. 19729548.8, dated Feb. 2, 2023, 5 pages.

* cited by examiner

DEVICE FOR FACILITATING THE FORMATION OF NEW BONE TISSUE

TECHNICAL FIELD

The present disclosure relates to a device for facilitating the formation of new bone tissue. More specifically, the disclosure relates to a device that makes it possible to make new bone tissue regrow starting from a condition in which the available bone tissue is in very small quantities.

BACKGROUND

As is known, the human skeleton is made up of bones and joints. The increase in weight caused by a sedentary lifestyle, the increasing age and the like all facilitate the spread of diseases such as arthrosis.

Thus artificial joints were created, prostheses which are inserted between two bone components to replace the natural joint. Initially the bond between the prosthesis and the two bone components is made using cement. Later, cement-free joint prostheses were used, in which the artificial joint is made with osteoinductive materials and coverings. A particular category of artificial prostheses is represented by prostheses for "major disasters": these are prostheses used in cancer patients or in patients undergoing multiple interventions to overhaul previous prostheses. In both cases, the available bone tissue is in very reduced quantities.

Usually in cement-free prostheses, efforts are made to increase the area of contact between the prosthesis and the bone to the maximum. In prostheses for "major disasters", in addition to seeking the largest area of contact, efforts are made to take advantage of the requirements of fibrocartilage callus.

Fibrocartilage callus, which acts as repair tissue, is a typical condition that arises after a trauma (such as the removal of bone tissue affected by a tumor) or fracture. About four weeks after the traumatic event, the first signs appear of callogenesis, i.e. the new tissue which is formed knits the two stumps, and with the passing of time it changes in response to the mechanical forces that are exerted on it, gradually becoming increasingly strong and resistant.

In particular, there is periosteum callus, which develops peripherally, and endosteal callus, which forms in the medullary cavity.

SUMMARY

The aim of the present disclosure is to provide a device for facilitating the formation of new bone tissue that can be inserted into the medullary canal of a bone.

Within this aim, the present disclosure provides a device for facilitating the formation of new bone tissue which favors the formation of periosteum callus externally and of endosteal callus internally.

The present disclosure also provides a device for facilitating the formation of new bone tissue, in the condition where the available bone tissue is in very small quantities.

The present disclosure further provides a device for facilitating the formation of new bone tissue that can be used or positioned at the apex of stump of available bone.

The present disclosure also provides a device for facilitating the formation of new bone tissue that is highly reliable, easily and practically implemented and of low cost.

This aim and these and other advantages which will become better apparent hereinafter are achieved by providing a device for facilitating the formation of new bone tissue, characterized in that it comprises a body that defines an upper portion and a lower portion, said lower portion having a substantially frustum shape, said upper portion having a substantially cylindrical shape, said lower portion being adapted to be inserted into the medullary canal of a bone.

BRIEF DESCRIPTION OF THE DRAWINGS

Further characteristics and advantages of the disclosure will become better apparent from the description of a preferred, but not exclusive, embodiment of the device according to the present disclosure, which is illustrated by way of non-limiting example in the accompanying drawings wherein.

DETAILED DESCRIPTION OF THE DRAWINGS

Figure 1:
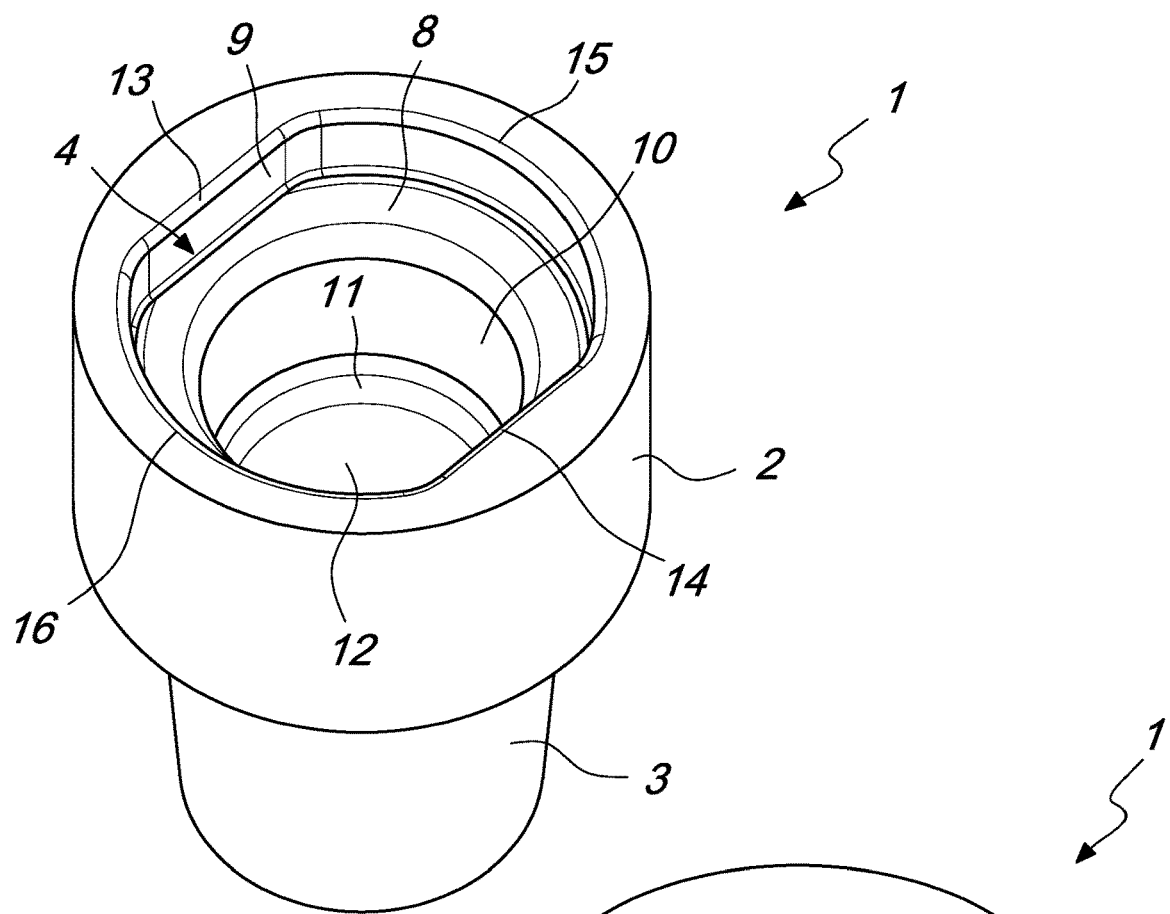
FIG. 1 is a perspective view from above of the device according to the disclosure.
Figure 2:
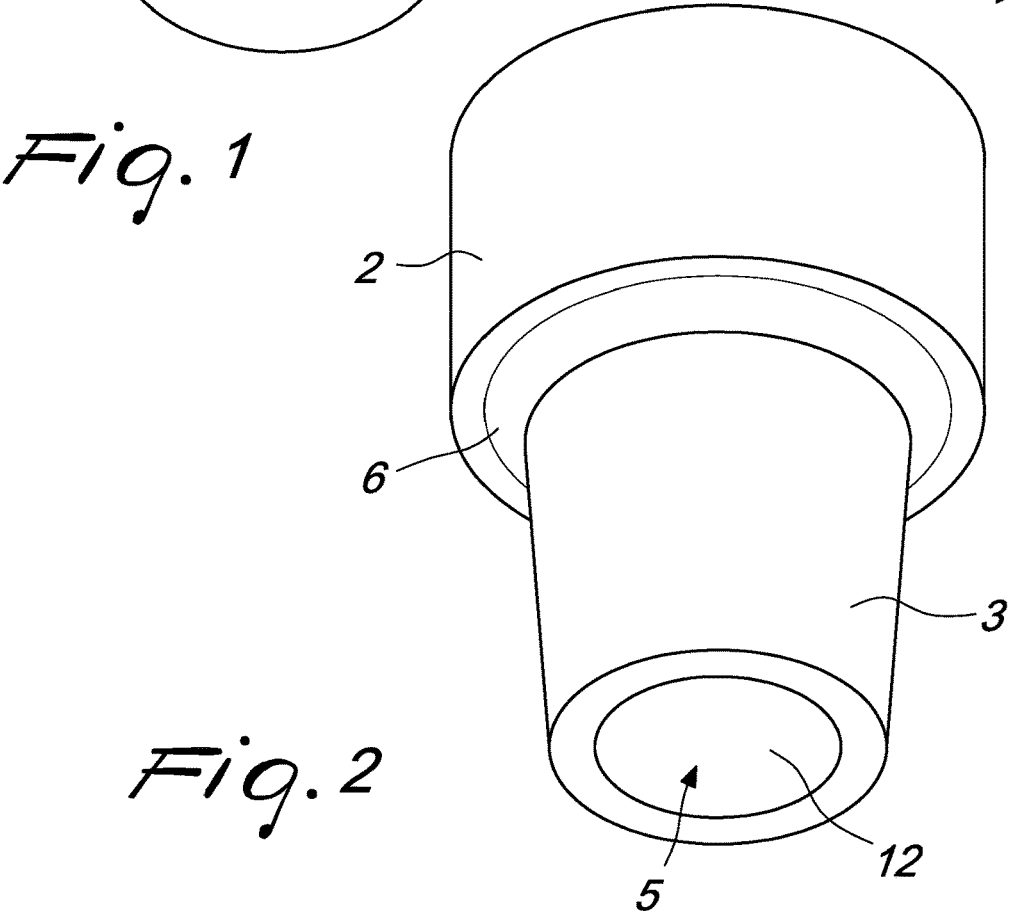
FIG. 2 is a perspective view from below of the device according to the disclosure.
Figure 3:
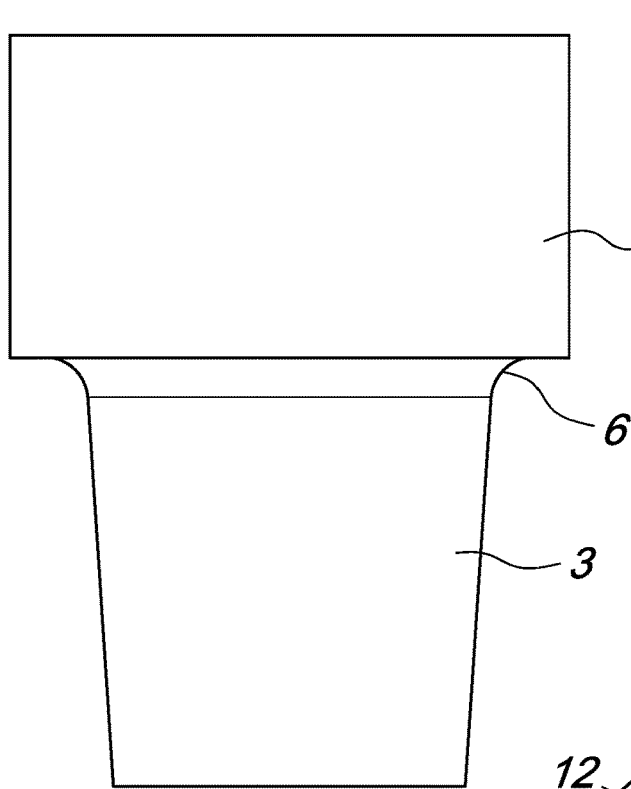
FIG. 3 is a side view of the device according to the disclosure.
Figure 5:
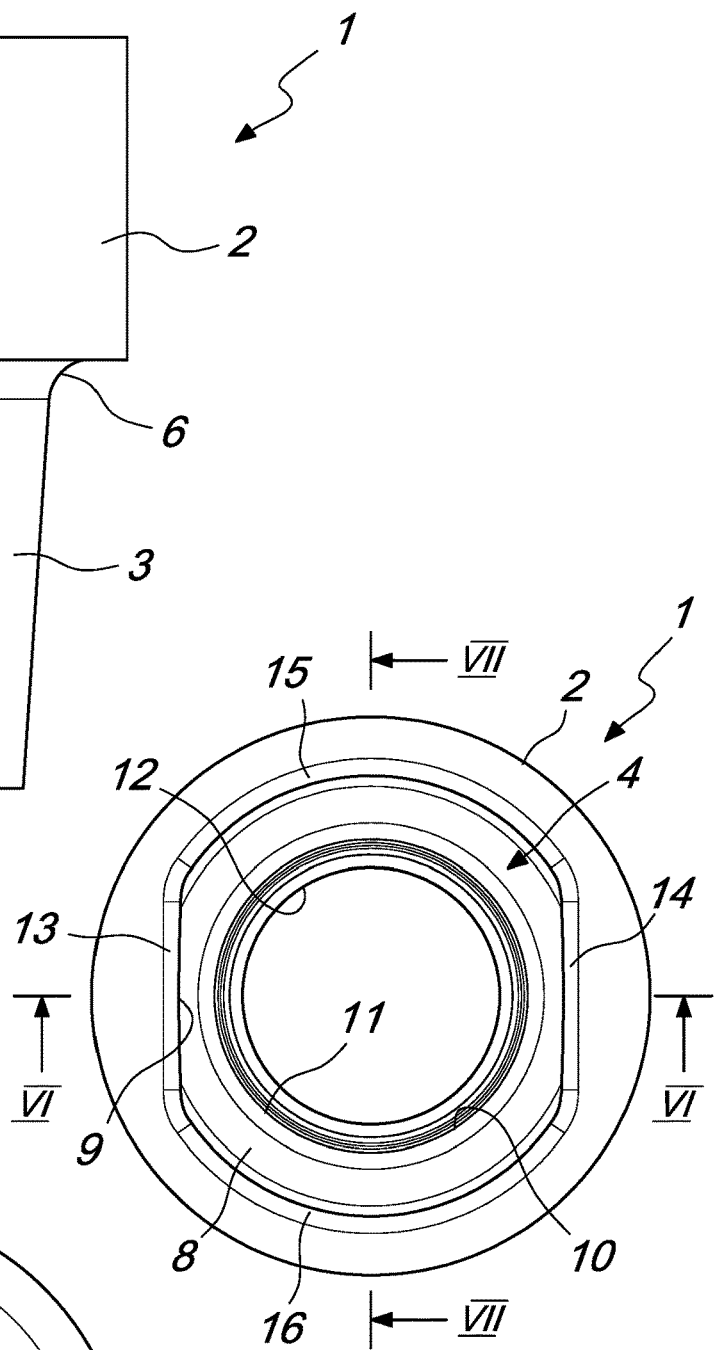
FIG. 5 is a plan view from above of the device according to the disclosure.
Figure 4:
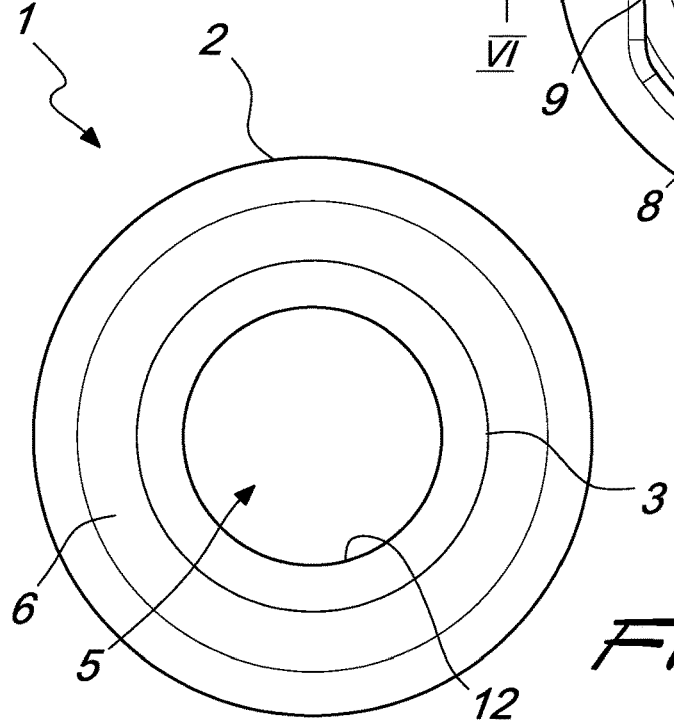
FIG. 4 is a plan view from below of the device according to the disclosure.
Figure 6:
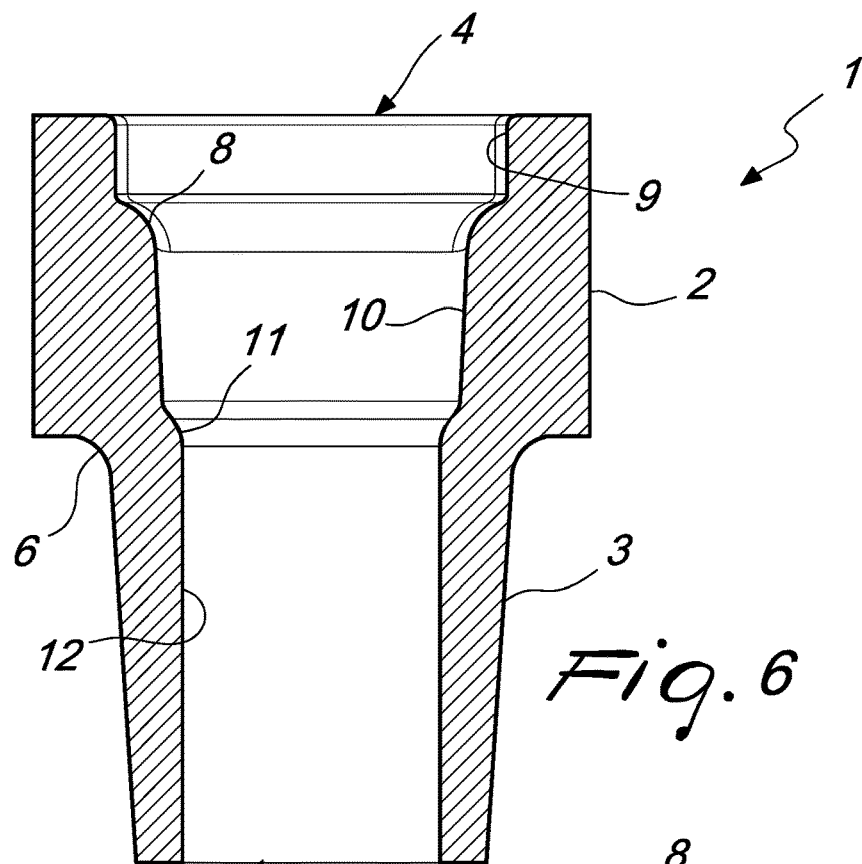
FIG. 6 is a cross-sectional view of the device according to the disclosure taken along the line VI-VI.
Figure 7:
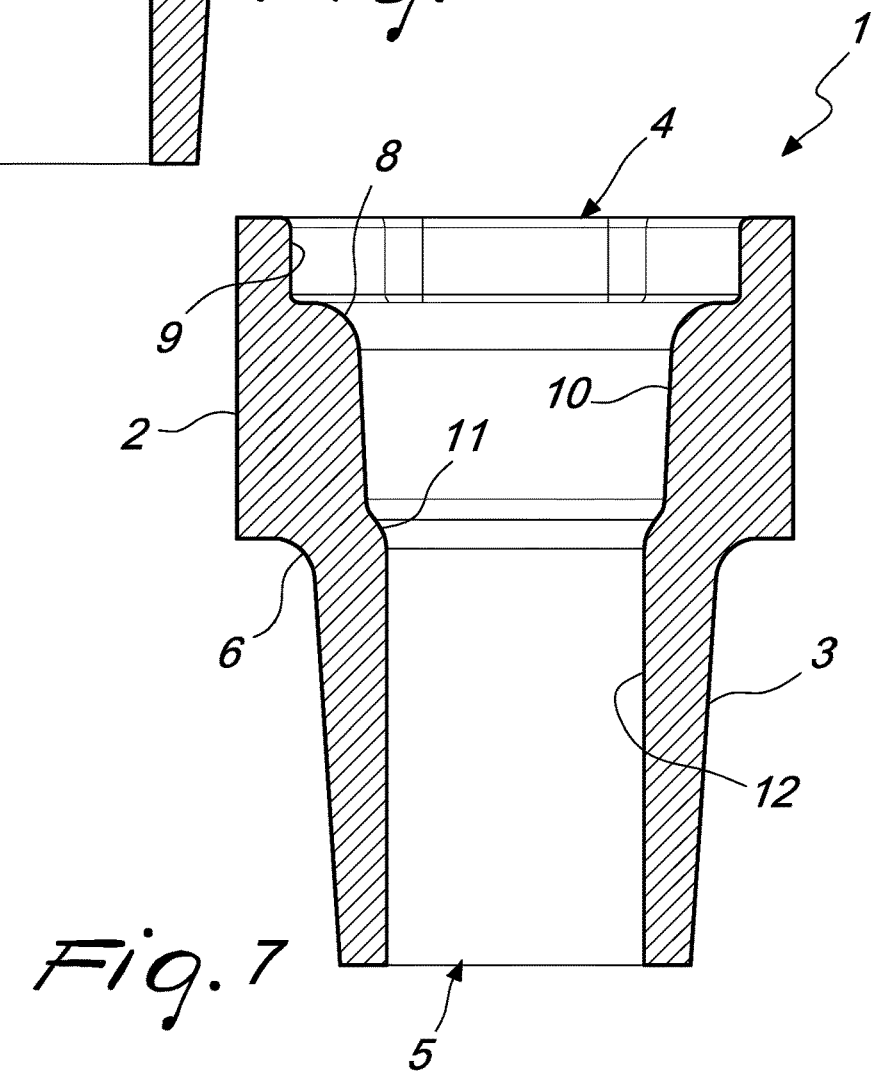
FIG. 7 is a cross-sectional view of the device according to the disclosure taken along the line VII-VII.

With reference to the figures, the device according to the present disclosure, generally designated by the reference numeral 1, comprises an upper portion 2 and a lower portion 3. The distinction between the lower part 3 and the upper part 2 is to indicate the part (lower) that is adapted to be inserted into the medullary canal of a bone, thus distinguishing it from the upper portion 2 which is adapted to protrude from the medullary canal.

Advantageously, the device according to the disclosure is configured as an internally hollow body, with a top opening 4 and a bottom opening 5.

Conveniently, the lower portion 3 of the device according to the disclosure is frustum-shaped, in order to allow the insertion into the medullary canal. By contrast, the upper portion 2 is made in a substantially cylindrical or conical shape.

This facilitates not only the formation of periosteal callus (at the upper part) but also of endosteal callus (at the frustum-shaped lower part), thus overcoming the limitations of the known art.

Conveniently the upper portion 2 is blended with the lower region 3 with a curved segment 6.

Advantageously the upper portion 2, hollow, is internally contoured in steps toward the axis of the body, so as to define, downward from above, i.e. from the upper portion 2 toward the lower portion 3, a first step 8 which connects a first upper portion 9 to a second upper portion 10, by way of a curved portion, and a second step 11 which connects the second upper portion 10 to the inner surface 12 of the lower portion 3.

The inner surface 12 of the lower portion 3 is cylindrical.

The top opening 4 is conveniently shaped with two straight and parallel sections which are connected by two curved sections 15 and 16.

The device according to the disclosure is provided by means of additive technology starting from titanium alloy powder, or chrome-cobalt molybdenum alloy powder, materials that are particularly suitable to facilitate bone regrowth.

By way of such technique and such materials it is possible to obtain a porous outer surface that is capable of facilitating the formation of new bone tissue.

The device according to the disclosure is adapted to be positioned at the apex of a stump of available bone, and takes advantage of the two types of fibrocartilage callus, i.e:

- external (periosteal) fibrocartilage callus developing between the outer bone and the upper portion 2 (cylindrical or conical in shape) of the device according to the disclosure;
- internal (endosteal) fibrocartilage callus developing between the lower portion 3 (frustum in shape) of the device according to the disclosure, which is inserted into the medullary canal of the bone, and the endosteal bone of the diaphyseal cavity.

In this manner, a kind of connecting portion between the external fibrocartilage callus and the internal fibrocartilage callus is achieved by way of the device according to the disclosure.

The device enables a high level of osseointegration, and makes it possible to intervene in those patients whose quantity of bone is very low as a consequence of major removals of bone or as a consequence of multiple overhaul interventions.

The device, thus conceived, is susceptible of numerous modifications and variations, all of which are within the scope of the appended claims.

Moreover, all the details may be substituted by other, technically equivalent elements.

In practice, the materials used, as well as the contingent shapes and dimensions, may be any according to the requirements and to the state of the art.

The disclosures in Italian Patent Application No. 102018000007049 from which this application claims priority are incorporated herein by reference.

The invention claimed is:

1. A device for facilitating the formation of new bone tissue, the device comprising: a body that defines an upper portion and a lower portion, said lower portion having a substantially frustum shape, said upper portion having a substantially cylindrical shape, said lower portion being adapted to be inserted into a medullary canal of a bone, wherein said body is an internally hollow body which has a top opening and a bottom opening, said device being provided by an additive powder technology, wherein said lower portion and said upper portion of the body have a porous outer surface configured to facilitate osseointegration, wherein said upper portion is internally contoured in steps toward an axis of the body, so as to define, from the upper portion toward the lower portion, a first step which connects a first inner upper portion to a second inner upper portion, by way of an inner curved portion, said first step defined by the inner curved portion protruding inside the hollow body with a convex portion, and a second step which connects the second inner upper portion to an inner surface of the lower portion, said second step being also defined by an inner curved portion protruding inside the hollow body with a convex portion, and wherein said upper portion is blended with said lower portion with a curved concave segment.

2. The device according to claim 1, wherein the device is coated with hydroxyapatite.

3. The device according to claim 1, wherein the device is configured to be positioned at the apex of stump of available bone.

4. The device according to claim 1, wherein said lower portion has a smaller diameter than said upper portion.

\* \* \* \* \*